US00PP14583P29

(12) United States Plant Patent
Zaiger et al.

(10) Patent No.: US PP14,583 P2
(45) Date of Patent: Mar. 9, 2004

(54) INTERSPECIFIC TREE NAMED: 'SPLASH'

(50) Latin Name: *Prunus salicina*
Varietal Denomination: Splash

(76) Inventors: Gary Neil Zaiger, 1907 Elm Ave., Modesto, CA (US) 95358; Grant Gene Zaiger, 4005 California Ave., Modesto, CA (US) 95358; Leith Marie Gardner, 1207 Grimes Ave., Modesto, CA (US) 95358

( * ) Notice: Subject to any disclaimer, the term of this patent is extended or adjusted under 35 U.S.C. 154(b) by 0 days.

(21) Appl. No.: 10/422,575

(22) Filed: Apr. 25, 2003

(51) Int. Cl.[7] ..... A01H 5/00
(52) U.S. Cl. ..... Plt./180
(58) Field of Search ..... Plt./180

*Primary Examiner*—Anne Marie Grunberg

(57) ABSTRACT

A new and distinct variety of interspecific tree [(*Prunus salicina*×(*Prunus salicina*×*Prunus armeniaca*))×(*Prunus salicina*×*Prunus armeniaca*)]. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Heavy and regular bearer of fruit.
2. Fruit with excellent flavor and eating quality.
3. Fruit with relatively uniform size throughout the tree.
4. Fruit that is moderately juicy with good balance between acid and sugar.
5. Fruit with a high Brix of 18°.
6. Fruit holding firm on the tree 12 to 15 days after maturity (shipping ripe).

1 Drawing Sheet

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries and interspecifics are exemplary. It was against this background of our activities that the present variety of interspecific tree was originated and asexually reproduced by us in our experimental orchard located near Modesto, Stanislaus County, Calif.

PRIOR VARIETIES

Among the existing varieties of plum trees, which are known to us, and mentioned herein, are 'Friar' Plum (non-patented) 'Red Beaut' Plum (U.S. Plant Pat. No. 2,539).

STATEMENT REGARDING FEDERALLY SPONSORED RESEARCH AND DEVELOPMENT

Not applicable.

ORIGIN OF THE VARIETY

The new and distinct variety of interspecific tree [(*Prunus salicina*×(*Prunus salicina*×*Prunus armeniaca*))×(*Prunus salicina*×*Prunus armeniaca*)] was originated by us in our experimental orchard, located near Modesto, Calif., as a first generation cross between our proprietary parents, with field identification numbers 29EB323 and 4G1180. The maternal parent (29EB323) originated from a cross of 'Friar' Plum (non-patented) with a proprietary plumcot identified as 4G1180, which was selected from open pollinated, seedlings grown from 'Red Beaut' Plum (U.S. Plant Pat. No. 2539), that had crossed with an apricot of unknown parentage. The paternal parent was pollen of the same proprietary plumcot (4G1180). We planted and maintained a large number of these first generation seedlings, growing on their own root system, under close observation, during which time the present new seedling exhibited distinct and desirable fruit and tree characteristics was selected in 1987 for asexual propagation and commercialization.

ASEXUAL REPRODUCTION OF THE VARIETY

Asexual reproduction of the new and distinct variety of interspecific tree was by budding, in 1990, to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE VARIETY

The present variety of interspecific tree is of large size, upright growth and a productive and regular bearer of small to medium size, firm, yellow flesh fruit with excellent flavor and eating quality. The fruit is further characterized with being moderately juicy with a good balance between acid and sugar, holding firm on the tree after maturity for 12 to 15 days, in comparison to the 'Red Beaut' Plum (U.S. Plant Pat. No. 2,539), the tree has heavier production, the fruit is higher in Brix, has greater eating quality, has yellow skin color compared to red and is approximately 28 days later in maturity. In comparison to 'Friar' Plum (non-patented), the fruit is higher in Brix, has greater eating quality and is approximately 35 days earlier in maturity.

PHOTOGRAPH OF THE VARIETY

The accompanying color photographic illustration shows typical specimens of the foliage and fruit of the present new interspecific variety. The illustration shows the upper and lower surface of the leaves, an exterior and sectional view of a fruit divided in its suture plane to show flesh color, pit cavity and the stone remaining in place. The photographic illustration was taken shortly after being picked (shipping ripe) and the colors are as nearly true as is reasonably possible in a color representation of this type.

DESCRIPTION OF THE VARIETY

The following is a detailed botanical description of the variety of interspecific tree, its flowers, foliage and fruit, as based on observations of 6 year old specimens grown near Modesto, Calif., with color in accordance with Munsell Book of Color.

Tree:

*Size.*—Large, pruned to 3 to 3.5 meters in height for economical harvesting of fruit.

*Vigor.*—Vigorous, growth of 1.5 to 2 meters in height the first growing season. Varies with soil type, fertility, and climatic conditions.

*Form.*—Upright, becomes more spreading with heavy crop load. Typical of plum growth.

*Branching Habit.*—Upright, crotch angle approximately 30°, increases with weight of fruit.

*Productivity.*—Heavy, thinning and spacing of fruit necessary.

*Bearer.*—Regular. Three consecutive years of adequate fruit set, no alternate bearing observed.

*Fertility.*—Self sterile, pollenizer required.

*Density.*—Medium dense. Usually pruned to vase shape to allow more sunlight to center of tree to increase Brix and keep fruit wood healthy.

*Hardiness.*—Hardy in all fruit growing areas of California. Approximate winter chilling requirement 650 hours at or below 45° F.

Trunk:

*Size.*—Large. Average circumference of 39.6 cm at 25.0 cm above ground on a 6 year old tree.

*Texture.*—Medium shaggy, gets rougher with age.

*Color.*—Varies from 10YR 7/2 to 5YR 6/6.

Branches:

*Size.*—Average circumference 11.1 cm at 65.8 cm above ground.

*Surface Texture.*—New growth smooth, becoming medium rough on more mature growth.

*Lenticels.*—Average number of 43 in a 25.8 square cm section. Average length 3.5 mm. Average width 1.8 mm. Color — 2.5YR 6/8.

*Color.*—New growth varies from 5R 5/6 when exposed to direct sunlight to 2.5GY 6/6 when in full shade. Old growth 7.5R 5/4, becomes darker with age.

Leaves:

*Size.*—Medium. Average length 88.9 mm. Average width 40.2 mm.

*Form.*—Oblanceolate.

*Apex.*—Acuminate.

*Base.*—Cuneate.

*Margin.*—Doubly serrate.

*Thickness.*—Medium.

*Surface texture.*—Upper surface relatively smooth, slight indentation over midrib and leaf veins, glabrous. Lower surface relatively smooth, except for small ridges created by midrib and pinnate venation, glabrous.

*Petiole.*—Average length 14.5 mm. Average width 1.3 mm. Color varies from 5R 5/8 on upper portion to 2.5GY 7/6 for lower portion. Grooved longitudinally, glabrous.

*Glands.*—Globose. Small to medium in size. Average length 0.6 mm. Average width 0.3 mm. Color varies from 2.5GY 6/8 on lower portion to 2.5R 5/8 on top edges. Number varies from 1 to 3, average number 2. Located on upper portion of petiole and lower portion of leaf blade.

*Color.*—Upper surface varies from 2.5GY 6/10 to 5GY 3/4. Lower surface varies from 5GY 5/4 to 5GY 8/8.

*Midvein.*—Pronounced, extends into petiole. Color — 2.5GY 8/6.

Flower buds:

*Size.*—Small. Average length 8.8 mm. Average diameter 4.6 mm.

*Hardiness.*—Hardy in respect to California fruit growing areas.

*Form.*—Conical, becoming slightly elongated before opening.

*Pubescence.*—Glabrous.

*Pedicel.*—Long and thin. Average length 7.0 mm. Average width 0.6 mm. Color — 2.5GY 7/10.

*Color.*—N 9.5.

*Number of buds per spur.*—Varies from 5 to 15, average 9.

Flowers:

*Size.*—Small. Average height 10.6 mm. Average diameter 20.1 mm.

*Petals.*—Number 5, alternately arranged to sepals. Shape — ovate, narrows at point of attachment. Average length 8.8 mm. Average width 6.8 mm. Color N9.5/. Margin — entire, slightly cupped at apex.

*Sepals.*—Number 5, alternately arranged to petals. Shape — elongated, apex comes to slight point. Surface — both upper and lower surface glabrous. Average length 2.9 mm. Average width 2.2 mm. Color — lower surface 2.5Y6. Upper surface 5GY 5/8.

*Stamens.*—Average 29 per flower. Average filament length 5.9 mm. Filament color N 9.5/. Anther color 10R 5/8.

*Pollen.*—Self sterile, pollenizer required. Color 7.5YR 7/12.

*Pistil.*—Usually one. Average length 8.1 mm. Surface — glabrous. Height compared to stamens approximately 1.1 mm lower. Color 2.5GY 9/6.

*Fragrance.*—Slight to moderate aroma.

*Blooming period.*—Date of First Bloom Feb. 25, 2001. Date of Petal Fall Mar. 6, 2001. Varies slightly with climatic conditions.

*Color.*—N9.5/.

*Number flowers per flower bud.*—Usually 2, varies from 1 to 3.

*Pedicel.*—Average length 7.9 mm. Average width 0.7 mm. Color 2.5GY 8/12.

Fruit:

*Maturity when described.*—Firm ripe.

*Date of first picking.*—Jun. 21, 2001.

*Date of last picking.*—Jun. 27, 2001. Varies slightly with climatic conditions.

*Size.*—Small to medium. Average diameter axially 50.0 mm. Average transversely in suture plane 50.2 mm. Average weight 85.2 grams, varies slightly with fertility of the soil, amount of thinning and climatic conditions.

*Form.*—Globose. Slightly enlarged at apex.

*Suture.*—Shallow, extends from base to apex.

*Ventral surface.*—Smooth, some fruit slightly lipped.

*Apex.*—Varies from rounded to slight point.

*Base.*—Varies from flat to slightly retuse.

*Cavity.*—Rounded to slightly elongated in suture plane. Average depth 4.6 mm. Average breadth 7.2 mm.

Stem:

*Size.*—Medium. Average length 12.5 mm. Average diameter 2.3 mm.

*Color.*—Varies from 5Y 5/6 to 5Y 5/8.

Flesh:

*Ripens.*—Evenly.

*Texture.*—Firm, smooth, comparable to 'Red Beaut' Plum (U.S. Plant Pat. No. 2,539).

*Fibers.*—Few, small, tender.

*Aroma.*—Slight.

*Amydgalin.*—Undetected.

*Eating quality.*—Excellent.

*Flavor.*—Excellent, good balance between acid and sugar.

*Juice.*—Moderate, enhances flavor.

*Brix.*—18.0°, varies slightly with amount of fruit per tree and climatic conditions.

*Color.*—Varies from 2.5Y 9/4 to 2.5Y 8.5/6. Pit cavity varies from 10YR 8/6 to 10YR 7/8.

Skin:

*Thickness.*—Medium.

*Surface.*—Smooth.

*Bloom.*—Moderate, complete coverage.

*Tendency to crack.*—None.

*Color.*—Uniform, varies from 10YR 8/10 to 10YR 7/10.

*Tenacity.*—Tenacious to flesh.

*Astringency.*—Undetected.

Stone:

*Type.*—Clingstone.

*Size.*—Medium. Average length 20.8 mm. Average width 17.4 mm. Average thickness 10.2 mm.

*Form.*—Obovate.

*Base.*—Usually flat, varies from flat to rounded.

*Apex.*—Cuspidate. Small, average length 0.7 mm.

*Surface.*—Pitted lightly throughout, small groove on each side of suture.

*Sides.*—Varies from equal to unequal, with one side extending further from suture plane.

*Ridges.*—Very few, small, extending a short distance from base toward apex.

*Tendency to crack.*—None.

*Color.*—Varies from 10YR 6/6 to 10YR 6/8 when dry.

Kernal:

*Form.*—Ovate.

*Taste.*—Bitter.

*Viability.*—Viable, embryo developed.

*Size.*—Average length 11.6 mm. Average width 9.6 mm. Average thickness 4.8 mm.

*Skin.*—Color varies from 10YR 8/4 to 10YR 7/4 when dry.

Use:

*Dessert.*—Market — local and long distance.

Keeping quality: Fair, held firm 10 days in cold storage at 38° to 42° F. without internal breakdown of flesh or appreciable loss of flavor.

Shipping quality: Fair, showed slight skin discoloration with minimal scarring or flesh bruising during picking, packing and shipping trials.

Plant/fruit disease resistance/susceptibility: No specific testing for relative plant/fruit disease has been designed. Under close observation during planting, growing and harvesting of fruit, under normal cultural and growing conditions near Modesto, Calif., no particular plant/fruit disease resistance or susceptibility has been observed. Any variety or selection observed during indexing of plant characteristics with abnormal susceptibility is destroyed and eliminated from our breeding program.

The present new variety of interspecific tree, its flowers, foliage and fruit herein described may vary in slight detail due to climate, soil conditions and cultural practices under which the variety may be grown. The present description is that of the variety grown under the ecological conditions prevailing near Modesto, Calif.

We claim:

1. A new and distinct variety of interspecific tree, substantially as illustrated and described, characterized by its large size, vigorous, upright growth and being a regular bearer of yellow flesh fruit with excellent flavor and eating quality and in comparison to the 'Red Beaut' Plum (U.S. Plant Pat. No. 2,539), the tree has heavier production, fruit that are higher in Brix, having greater eating quality and approximately 28 days later in maturity.

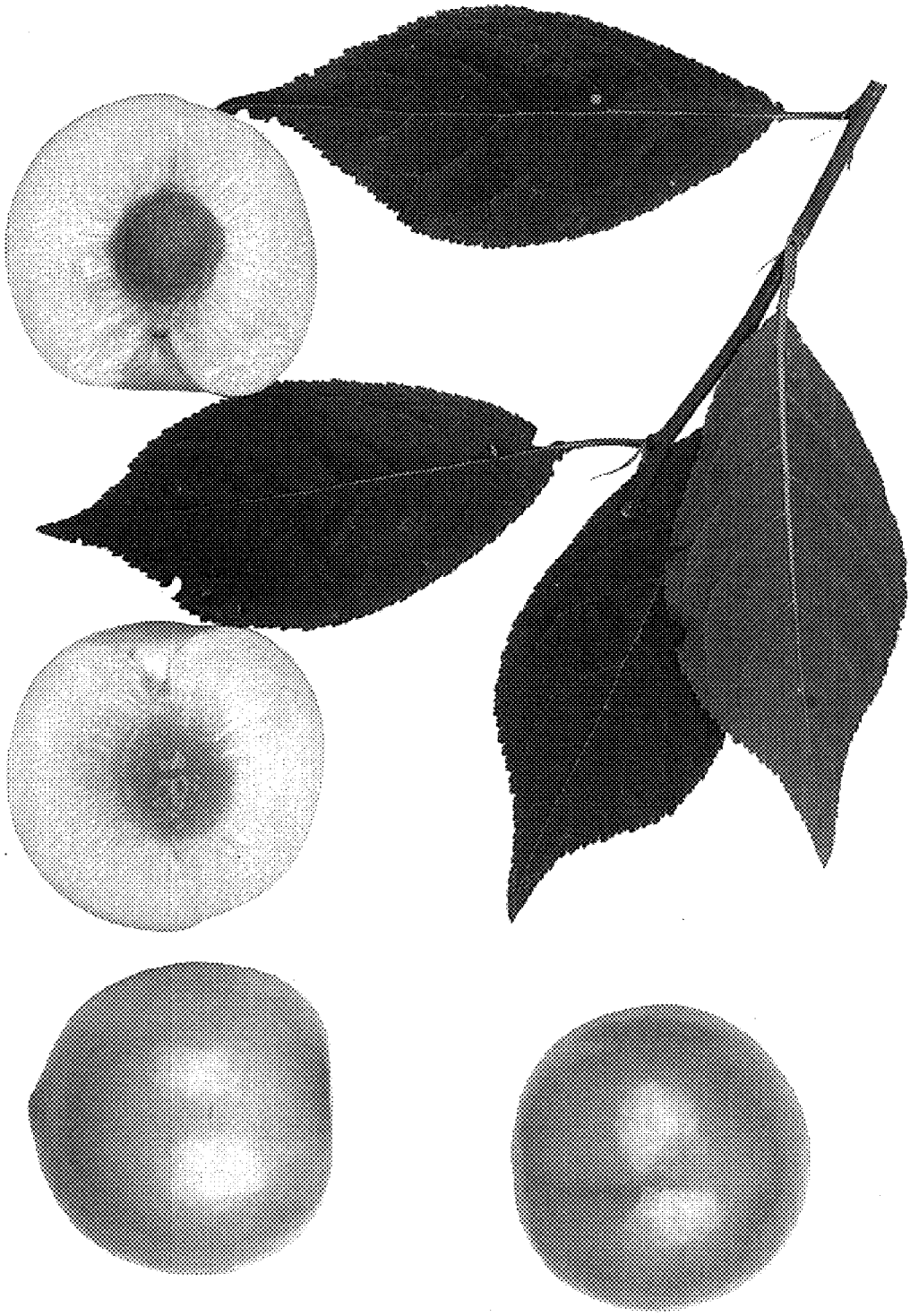

* * * * *